(12) United States Patent
Mohan et al.

(10) Patent No.: US 11,224,631 B2
(45) Date of Patent: Jan. 18, 2022

(54) READY-TO-USE CARFILZOMIB COMPOSITIONS

(71) Applicant: Orbicular Pharmaceutical Technologies Pvt. Ltd., Telangana (IN)

(72) Inventors: Mailatur Sivaraman Mohan, Telangana (IN); Hiren Patel, Telangana (IN); Bhaveshkumar Vallabhbhai Patel, Telangana (IN); Raghu Kannekanti, Telangana (IN); Mohammad Raheesh, Telangana (IN)

(73) Assignee: Orbicular Pharmaceutical Technologies Pvt. Ltd.

( * ) Notice: Subject to any disclaimer, the term of this patent is extended or adjusted under 35 U.S.C. 154(b) by 0 days.

(21) Appl. No.: 16/480,561

(22) PCT Filed: Apr. 25, 2017

(86) PCT No.: PCT/IB2017/052359
§ 371 (c)(1),
(2) Date: Jul. 24, 2019

(87) PCT Pub. No.: WO2018/138557
PCT Pub. Date: Aug. 2, 2018

(65) Prior Publication Data
US 2019/0351007 A1    Nov. 21, 2019

(30) Foreign Application Priority Data
Jan. 24, 2017  (IN) .............................. 201741002669

(51) Int. Cl.
| | | |
|---|---|---|
| *A61K 38/07* | (2006.01) |
| *A61K 9/00* | (2006.01) |
| *A61K 47/10* | (2017.01) |
| *A61K 47/12* | (2006.01) |

(52) U.S. Cl.
CPC ............ *A61K 38/07* (2013.01); *A61K 9/0019* (2013.01); *A61K 47/10* (2013.01); *A61K 47/12* (2013.01)

(58) Field of Classification Search
None
See application file for complete search history.

(56) References Cited

U.S. PATENT DOCUMENTS

| | | |
|---|---|---|
| 7,737,112 B2 | 6/2010 | Lewis et al. |
| 9,636,376 B2 | 5/2017 | Hippalgaonkar et al. |
| 10,098,890 B2 | 10/2018 | Shete et al. |
| 2014/0073583 A1 | 3/2014 | Hippalgaonkar et al. |

FOREIGN PATENT DOCUMENTS

| | | |
|---|---|---|
| IN | 02/2017 | 1/2017 |
| WO | 2015198257 A1 | 12/2015 |
| WO | 2016116882 A2 | 7/2016 |
| WO | 2016170489 A1 | 10/2016 |
| WO | 2018138556 A1 | 8/2018 |

OTHER PUBLICATIONS

Free Dictionary https://medical-dictionary.thefreedictionary.com/ready-to-use#:~:text=Able%20to%20be%20dispensed%20with,%C2%A9%202009%20Farlex%20and%20Partners.*
International Search Report for Application No. PCT/IB2017/052359 dated Oct. 23, 2017.

* cited by examiner

*Primary Examiner* — James H Alstrum-Acevedo
*Assistant Examiner* — Tara L Martinez
(74) *Attorney, Agent, or Firm* — Lerner, David, Littenberg, Krumholz & Mentlik, LLP

(57) ABSTRACT

The present invention provides a stable, non-aqueous, ready-to-use parenteral composition comprising: carfilzomib or pharmaceutically acceptable salt thereof, acidifying agent, optionally a surfactant, one or more solvents or co-solvents.

11 Claims, No Drawings

READY-TO-USE CARFILZOMIB COMPOSITIONS

CROSS REFERENCE TO RELATED APPLICATIONS

The present application is a national phase entry under 35 U.S.C. § 371 of International Application No. PCT/IB2017/052359, filed Apr. 25, 2017, which claims priority from India Patent Application No. 201741002669 filed Jan. 24, 2017, all of which are hereby incorporated herein by reference.

FIELD OF THE INVENTION

The present invention relates to a stable, non-aqueous, ready-to-use parenteral composition comprising: carfilzomib or pharmaceutically acceptable salt thereof, acidifying agent, optionally a surfactant, one or more solvents.

BACKGROUND OF THE INVENTION

Carfilzomib is a peptide epoxy ketone derivative, chemically, it is a tetra peptide epoxy ketone and an analog of epoxomicin. Carfilzomib is commercially available as KYPROLIS® (Carfilzomib for Injection, which is a lyophilized formulation available as 30 mg/vial and 60 mg/vial a sterile, white to off-white lyophilized powder and is available as a single-use vial. Each 30 mg vial of KYPROLIS contains 30 mg of Carfilzomib, 1500 mg sulfobutylether beta-cyclodextrin, and 28.9 mg anhydrous citric acid, and each 60 mg vial contains 60 mg of Carfilzomib, 3000 mg sulfobutylether beta-cyclodextrin, 57.7 mg citric acid, and sodium hydroxide for pH adjustment (target pH 3.5).

Due to stability issues, carfilzomib containing compositions must be lyophilized before storage and reconstituted before use. The reconstituted solution should be diluted further. The reconstituted or diluted compositions are not stable and must be used within 24 hours after reconstitution. It requires initial reconstitution, two dilutions prior to intravenous infusion and the same needs to be carried out under aseptic conditions.

Prior to administration, the KYPROLIS® (Carfilzomib) for Injection must first be reconstituted with 29 mL and 15 mL of sterile water for injection, which dilutes the amount of carfilzomib to 2 mg/mL, and then further withdraw the calculated dose from the vial and diluted into 50 mL using 5% dextrose Injection, USP intravenous bag.

The difficulties with the commercially available KYPROLIS ® (Carfilzomib) formulation is complex administration process involving multiple steps. As described above, the person administering the drug must first reconstitute the vial with sterile water for injection and then subsequently transfer the reconstituted solution into an intravenous bag. While reconstituting, the medical practitioner must gently swirl and/or invert the vial slowly for about 1 minute, or until complete dissolution of any cake or powder occurs. The prescribing information for KYPROLIS® (Carfilzomib) for Injection gives clear instructions not to shake the vial to avoid foaming. Possibility of foaming during reconstitution may pose risk of dosing error. A further difficulty of the KYPROLIS® (Carfilzomib) product is that the time duration from reconstitution to administration must be completed in 24 hours. Further all the above mentioned reconstitution steps need to be carried out in aseptic conditions, making the process still difficult to follow.

U.S. Pat. No. 7,737,112 discloses pharmaceutical compositions of practically insoluble proteasome inhibitors. The compositions disclosed in this patent utilize cyclodextrin, water and organic solvents in order to increase the solubility and stability of the practically insoluble proteasome inhibitors.

US patent application no. 20140073583 A1 discloses pharmaceutical compositions comprising peptide epoxy ketone, solvent suitable for injection selected from group consisting ethanol, propylene glycol, polyethylene glycol and mixtures thereof, optionally water and a non-volatile sugar acid as a lyophilized composition. Also disclosed is a liquid composition of carfilzomib.

WO patent publication 2015198257 A1 discloses a stable carfilzomib injection comprising carfilzomib or pharmaceutically acceptable salts thereof with citric acid, tertiary butyl alcohol and water for injection to obtain lyophilized product, wherein the said injection is free from cyclodextrin derivatives; further the invention also discloses a ready-to-use injection comprising carfilzomib, citric acid, dimethyl acetamide and polysorbate 80, and the injection is free from cyclodextrin derivatives.

WO patent publication 2016170489 A1 discloses pharmaceutical composition comprising carfilzomib or a pharmaceutically acceptable salt thereof, at least one organic solvent such as dimethylacetamide or propylene glycol or ethanol, and a solubilizer such as hydroxy propyl beta-cyclodextrin (HPBCD), the composition further comprises citric acid, wherein said composition has a water content of less than 2.5 percent w/w.

The marketed KYPROLIS® (Carfilzomib) product has many limitations, such as long manufacturing procedure including drug dissolution and long lyophilization cycle to obtain the lyophilized product. Further the lyophilized product requires multiple dilutions and the reconstituted or diluted composition develops frothing or foam formation, if proper care is not taken during reconstitution. If foam is formed, then the health professional needs to wait 5 minutes until the foam subsides from reconstituted solution. This is a cumbersome procedure and complication to health care professionals. Carfilzomib has low aqueous solubility and hence considering the above drawbacks, surprisingly a stable, ready-to-use, parenteral composition of carfilzomib has been developed using the non-aqueous environment which overcomes the above drawbacks. Further it does not require such cumbersome and expensive procedures of lyophilization, multiple dilutions and foaming.

SUMMARY OF THE INVENTION

The present invention relates to a stable, non-aqueous, ready-to-use parenteral composition comprising: carfilzomib or pharmaceutically acceptable salt thereof, acidifying agent, optionally a surfactant, one or more solvents.

The composition according to above aspect, wherein the acidifying agents include but not limited to sulphuric acid, hydrochloric acid, hydrobromic acid, phosphoric acid, ethanoic acid, boric acid, hydrofluoric acid, oxalic acid, nitric acid and the like;

surfactant include but not limited to polyoxyethylene sorbitan esters (tweens), polyoxyethylene polyoxypropylene copolymers (pluronics), sorbitan esters, lecithin, cremophor and mixtures thereof;

solvents include but not limited to glycols such as propylene glycol, polyethylene glycol and the like; alcohols such as ethanol, butanol, t-butanol; glycerol or its derivatives and mixtures thereof;

Another aspect relates to a stable, non-aqueous, ready-to-use parenteral composition comprising:
i. carfilzomib or pharmaceutically acceptable salt thereof in a concentration range of about of 1 mg/mL to about 20 mg/mL,
ii. acidifying agent selected from ethanoic acid in a specific ratio of about 1:1 and less than or equal to about 15:1,
iii. optionally surfactants, and
iv. solvents selected from propylene glycol, polyethylene glycol, ethanol.

The composition according to preceding claims, the composition may comprise other excipients such as antioxidants and/or preservatives optionally.

The composition according to according to above aspect, wherein the ratio of ethanoic acid to carfilzomib is between about 1.5:1 to about 10:1.

The composition according to previous aspects, the composition is free of cyclodextrins, water and non-volatile sugar acid.

The composition according to previous aspects, wherein the pH of the composition is from about 2 to about 9.

The non-aqueous composition according to preceding claims for administering carfilzomib in patients in need thereof for the treatment of multiple myeloma and related conditions.

One more aspect of the invention relates to the process for the preparation of a composition, comprising:
a) add required quantity of ethanol in a manufacturing vessel and add carfilzomib to it and stir to obtain a clear solution,
b) to the above vessel optionally other solvents propylene glycol or polyethylene glycol, and optionally polysorbate or sorbitan esters and optionally antioxidant may be added,
c) adjust the pH using suitable acidifying agent,
d) filter and fill the filtered solution into vials, stopper and seal the vials and store the vials in suitable shipper,
e) inert gas such as nitrogen is used throughout the process to reduce the risk of oxidation of carfilzomib.

DETAILED DESCRIPTION OF THE INVENTION

The term "composition" is intended to encompass a combination including active ingredients and pharmaceutically acceptable excipients, as well as any product which results, directly or indirectly, from combination, complexation, or aggregation of any two or more of the ingredients, or from dissociation of one or more of the ingredients, or from other types of reactions or interactions involving one or more of the ingredients.

The term "formulation" or "dosage form" or "composition" refers to finished pharmaceutical products that are suitable for administration, including, but not limited to, injections, parenterals, etc.

The term "excipient" or "pharmaceutically acceptable excipient" or "adjuvant" means a component of a pharmaceutical product that is not a pharmacologically active ingredient, such as fillers, diluents, carrier, solvents, co-solvents, preservatives, buffers, bulking agents, sugars, cellulose and its derivatives, pH modifiers, antioxidants, surfactants, isotonicity agents, etc, added to a drug to increase or aid its effect. The excipients or adjuvants that are useful in preparing pharmaceutical compositions are generally safe, non-toxic, and neither biologically nor otherwise undesirable, and are acceptable for human pharmaceutical use as well as veterinary use. The term includes one or more excipients or adjuvants.

"Carrier" or "solvent" as used herein refers to pharmacologically inert materials that provide a more or less fluid matrix, suitable for topical drug administration. Carriers and solvents herein include any such materials known in the art, which are nontoxic and do not interact with other components of a pharmaceutical composition or drug delivery system in a deleterious manner. The compositions of the present invention are particularly suitable for parenteral administration. Compositions suitable for parenteral dosage forms such as injectable such as intravenous, intramuscular or subcutaneous, implants and the like. Other parenteral ingredients used in the composition are generally those commonly used and recognized by persons skilled in the art of parenteral formulations.

The term "Carfilzomib" includes the compound carfilzomib, pharmaceutically acceptable salts, esters, solvates, hydrates or polymorphs and the like thereof.

"Pharmaceutically-acceptable salts" refer to derivatives of the disclosed compounds wherein the parent compound is modified by making acid or base salts, solvate, hydrate and the like thereof. Pharmaceutically-acceptable salt forms of compounds provided herein are synthesized from the parent compound which contains a basic or acidic moiety by conventional chemical methods.

The term "optional" or "optionally" means that the subsequently described element, component or circumstance may or may not be present, so that the description includes instances where the element, component, or circumstance is included and instances where it is not.

The term "stable" or "stability" as used herein includes both physical and chemical stability. Stability parameters include but not limited to potency, related substances, stable pH value and other physico-chemical parameters.

The term "about" when used in conjunction with a numeral here refers to a range of that numeral +/−10%, inclusive. However, alternative concentrations are also expressly deemed suitable for use herein.

Non-aqueous refers to the property of being free or substantially free of water. However, this does not exclude the presence of residual amounts of water as commonly contained in non-aqueous organic liquids and residual amounts of water contributed from the process of manufacturing composition, such as trace amounts of moisture present in manufacturing vessels, tubing, filters and the like.

Any recitation of ranges of values set forth below is merely intended to serve as a shorthand method of referring individually to each separate value falling within the range, unless otherwise indicated herein, and each separate value is incorporated into the specification as if it were individually recited herein. Furthermore, all references, including patent applications, cited herein are hereby incorporated by reference to the same extent as if each reference were individually and specifically indicated to be incorporated by reference and were set forth in its entirety herein.

The present invention relates to a stable, non-aqueous, carfilzomib ready-to-use, parenteral composition, wherein the composition is free of non-volatile sugar acid, cyclodextrins and water.

The present composition can be prepared by combining carfilzomib, acidifying agent, and other excipients. The excipients include solvents, pH modifiers, preservatives, antioxidants, surfactant and the like or mixtures thereof The parenteral composition according to this invention wherein, examples of solvents include but not limited to glycols such as propylene glycol, butylene glycol, polyethylene glycol; polyethylene glycol include polyethylene glycol 300, polyethylene glycol 400 and the like; glycerol or its derivatives and mixtures thereof; dioxane, trioxane and other cyclic mono-, di- and tri-ethers, lower alkanols such as ethanol, propanol, isopropanol, sec-butanol, t-butyl alcohol (TBA), n-butyl alcohol, ethyl acetate, acetone, acetonitrile, ethoxy ethanol, methanol, N-methyl-2-pyrrolidone, glycofurol, glycerol formal, tetrahydrofurfuryl alcohol or other organic solvents and mixtures of suitable solvents thereof or their equivalents. Solvents or mixture or combination of solvents are used in a suitable proportion and suitable quantity to achieve desirable effect. Co-solvents may also be included in the present compositions and co-solvents include, but not limited to glycols such as propylene glycol, butylene glycol, polyethylene glycol and the like, polyethylene glycol include polyethylene glycol 300, polyethylene glycol 400 and the like; glycerol or its derivatives and mixtures thereof; dioxane, trioxane and other cyclic mono-, di- and tri-ethers, lower alkanols (such as ethanol, propanol, isopropanol, sec-butanol, t-butyl alcohol (TBA), n-butyl alcohol, ethyl acetate, acetone, acetonitrile, ethoxy ethanol, methanol, N-methyl-2-pyrrolidone, glycofurol, glycerol formal, tetrahydrofurfuryl alcohol or other organic solvents and mixtures of suitable solvents.

In another aspect the pH of the composition plays a significant role to keep the composition stable, pH of the present invention is from about 2 to about 9; further pH modifications are contemplated with suitable pH modifiers.

In one more aspect, by addition of acidifying agent to the composition, the pH of the composition was modified between about 2 to about 9 to obtain a clear stable solution after reconstitution.

The pH level for each pharmaceutical composition should be selected to provide suitable solubility of the active ingredient used therein. It is generally preferred, however, that the pH of the compositions be suitable for injection and, therefore, will typically be between about 2.0 and about 9.0. pH of the composition is modified to obtain a stable non-aqueous composition using suitable pH modifiers. pH of the present composition plays an important role in stabilizing the composition. By addition of acidifying agent to the composition, the pH of the composition was modified to obtain a clear stable solution after reconstitution.

In another aspect, the compositions are stable when the composition is added with pH modifiers, like acidifying agents. Examples of pH modifiers include but not limited to acidifying agents, such as but not limited to sulphuric acid, hydrochloric acid, phosphoric acid, ethanoic acid, boric acid, hydrofluoric acid, hydrobromic acid, oxalic acid, nitric acid or mixtures thereof. It is anticipated that upon addition of pH modifiers the composition is physically and chemically more stable than without those modifiers in the composition.

Further the composition may comprise of antioxidants and the antioxidants used in the compositions are optional. Examples of antioxidants include but not limited to monothioglycerol, alpha-tocopherol, L-cysteine, thioglycolic acid, sodium metabisulfite (SMBS), ascorbic acid, sodium formaldehyde sulfoxylate, sodium bisulfate, butylated hydroxy toluene (BHT), butylated hydroxy anisole (BHA) mixtures of combinations thereof.

In another aspect composition with antioxidants monothioglycerol, combination of butylated hydroxy toluene (BHT) and butylated hydroxy anisole (BHA), butylated hydroxy anisole (BHA), α-tocopherol, thioglycolic acid and composition without antioxidants were assessed using inert gas environment precautions. Considering the chemical stability with above antioxidants alpha-tocopherol, BHA and thioglycolic acid were found to be suitable in comparison with other antioxidants.

In another aspect the composition may comprise of surfactants. Examples of surfactant include tweens, tweens include but not limited to polyoxyethylene sorbitan esters such as polysorbate 20 (Tween 20), polysorbate 40 (Tween 40), and polysorbate 80 (Tween 80); polyoxyethylene polyoxypropylene copolymers such as pluronics; sorbitan esters such as sorbitan monostearate, sorbitan tristearate, sorbitan monolaurate and the like, lecithin, cremophor and mixtures thereof. Surfactants in the present compositions are optional and based on the requisite, the surfactants may be used.

The present invention may further comprise of other suitable excipients other than the disclosed excipients, excipients may include preservatives such as benzyl alcohol, thiomersal, butylated hydroxy toluene (BHT), butylated hydroxy anisole (BHA) and the like or mixtures thereof.

The present invention relates to a stable, non-aqueous, carfilzomib ready-to-use, parenteral composition, wherein the composition is free of non-volatile sugar acid, cyclodextrins and water.

The contemplated compositions are free of non-volatile sugar acid, cyclodextrins and water. Non-volatile sugar acid include citric acid, N-acetylneuraminic acid, N-acetyltalosaminuronic acid, aldaric acid, aldonic acid, 3-deoxy-D-manno-oct-2-ulosonic acid, galaturonic acid, D-galacturonic acid, glucaric acid, gluconic acid, glucuronic acid, glucono-gamma-lactone, glyceric acid, N-glycolylneuraminic acid, iduronic acid, isosaccharinic acid, lactobionic acid, mucic acid, muramic acid, neuraminic acid, pangamic acid, saccharic acid, sialic acid, threonic acid, ulosonic acid, uronic acid, X-Gluc, xylonic acid, ascorbic acid, mixtures thereof and other sugar acids, lactic acid, succinic acid, maleic acid, tartaric acid, salicylic acid, benzoic acid, methanesulfonic acid, oxalic acid, thioglycolic acid, and the like or mixtures thereof.

Cyclodextrins include alpha-, beta-, or gamma-cyclodextrins, beta-cyclodextrins include, hydroxy-alkyl beta-cyclodextrin, hydroxy-propyl-beta-cyclodextrin, sulfobutyl-ether-beta-cyclodextrin and the like. Further, the composition is free or substantially free of water, however, this does not exclude the presence of residual amounts of water as commonly contained in non-aqueous organic liquids and residual amounts of water contributed from the process of manufacturing composition, such as trace amounts of moisture present in manufacturing vessels, tubing, filters and the like. Therefore, the composition may comprise trace amounts of water coming from above process.

In another aspect the present invention relates to a stable, non-aqueous, carfilzomib ready-to-use, parenteral composition, wherein the composition comprises of:
i) carfilzomib or its pharmaceutically acceptable salts, solvates and hydrates thereof,
ii) acidifying agent selected from ethanoic acid in a specific ratio of about 1:1 and less than or equal to about 15:1
iii) solvents or co-solvents selected from propylene glycol, polyethylene glycol, ethanol, and
iv. optionally surfactants.

The non-aqueous solvent system includes, ethanol or propylene glycol or polyethylene glycol, or a mixture of one or more solvents, ethanol and propylene glycol; ethanol and polyethylene glycol; propylene glycol and polyethylene glycol; ethanol, propylene glycol and polyethylene glycol or any mixtures or combinations thereof. The composition may also comprise propylene glycol or polyethylene glycol, glycerol, dioxane, alcohol and the like as co-solvents.

In another aspect, the parenteral composition accordingly has concentration of carfilzomib between about 1 mg/mL to about 20 mg/mL; for example, between about 4 mg/mL to about 16 mg/mL and between about 6 mg/mL to about 12 mg/mL and composition is a ready-to-use composition.

In another aspect wherein the ratio of ethanoic acid to carfilzomib is between about 1:1 and less than or equal to about 15:1; for example, the ratio is between about 1.5:1 to about 10:1; further the ratio is between about 2:1 to about 8:1.

In another aspect the composition is free from lyophilization and the composition is a ready-to-use liquid solution, ready-to-use liquid concentrate, ready-to-dilute liquid solution, ready-to-dilute liquid concentrate and the like. A ready-to-use or ready-to-dilute liquid solution or liquid concentrate is a composition that is suitable for administration after dilution with a suitable diluent or physiological solution.

In another embodiment, the present invention relates to a stable, non-aqueous, ready-to-use, parenteral composition, comprising carfilzomib or its pharmaceutically acceptable salt thereof, ethanol, propylene glycol or derivatives, or polyethylene glycol derivatives thereof, pH modifier, optionally antioxidants, and optionally surfactants.

In another embodiment, the present invention relates to a stable, non-aqueous, ready-to-use, parenteral composition, comprising carfilzomib or its pharmaceutically acceptable salt thereof, ethanol, propylene glycol or derivatives thereof, polyethylene glycol 300 or polyethylene glycol 400 or derivatives thereof, acidifying agent such as ethanoic acid, optionally antioxidants and optionally surfactants.

In another embodiment, the present invention relates to a stable, non-aqueous, ready-to-use, parenteral composition, comprising carfilzomib or its pharmaceutically acceptable salt thereof, ethanol, propylene glycol or derivatives thereof, polyethylene glycol 300 or polyethylene glycol 400 or derivatives thereof, ethanoic acid, optionally polysorbate 80 and optionally thioglycolic acid or alpha-tocopherol or mixtures thereof.

In another embodiment, the present invention relates to a stable, non-aqueous, ready-to-use, parenteral composition, comprising carfilzomib or its pharmaceutically acceptable salt thereof, ethanol, ethanoic acid, optionally polysorbate 80 and optionally thioglycolic acid or alpha-tocopherol or mixtures thereof.

In another embodiment, the present invention relates to a stable, non-aqueous, ready-to-use, parenteral composition, comprising carfilzomib or its pharmaceutically acceptable salt thereof, ethanol, optionally polysorbate 80, acidifying agent and optionally butylated hydroxy toluene or butylated hydroxy anisole, or mixtures thereof.

In another embodiment, the present invention relates to a stable, non-aqueous, ready-to-use, parenteral composition, comprising carfilzomib or its pharmaceutically acceptable salt thereof, ethanol, optionally propylene glycol and/or polyethylene glycol 300 or polyethylene glycol 400 or derivatives thereof, ethanoic acid, optionally polysorbate or sorbitan esters and optionally thioglycolic acid or alpha-tocopherol.

In another embodiment, the present invention relates to a stable, non-aqueous, ready-to-use, parenteral composition, comprising carfilzomib or its pharmaceutically acceptable salt thereof, ethanol, optionally propylene glycol, polyethylene glycol 300 or polyethylene glycol 400 or derivatives thereof, thioglycolic acid or alpha-tocopherol, acidifying agent, optionally tweens or sorbitan esters, wherein the composition is free of non-volatile sugar acid, cyclodextrins and water.

In another embodiment, the present invention relates to a stable, non-aqueous, ready-to-use, parenteral composition, comprising carfilzomib or its pharmaceutically acceptable salt thereof, ethanol, optionally alpha-tocopherol, sulphuric acid, optionally tweens or sorbitan esters.

In another embodiment, the present invention relates to a stable, non-aqueous, ready-to-use, parenteral composition, comprising carfilzomib or its pharmaceutically acceptable salt thereof, ethanol, optionally alpha-tocopherol, ethanoic acid, optionally tweens or sorbitan esters.

In another embodiment, the present invention relates to a stable, non-aqueous, ready-to-use, parenteral composition, comprising carfilzomib or its pharmaceutically acceptable salt thereof, ethanol, optionally propylene glycol, optionally polyethylene glycol 300 or polyethylene glycol 400 or derivatives thereof, optionally alpha-tocopherol, ethanoic acid, optionally tweens or sorbitan esters, wherein the composition is free of non-volatile sugar acid, cyclodextrins and water.

In another embodiment, the present invention may further comprise of other suitable excipients to make a stable non-aqueous composition, wherein the composition is free of non-volatile sugar acid, cyclodextrins and water.

In another embodiment this invention discloses a process to prepare the ready-to-use stable parenteral composition which comprises of:

a) adding required quantity of ethanol in a manufacturing vessel and add carfilzomib to it and stir to obtain a clear solution, b) to the above vessel optionally other solvents propylene glycol or polyethylene glycol, and optionally polysorbate or sorbitan esters and optionally antioxidant may be added, c) adjusting the pH using suitable acidifying agent, d) filtering the solution, filling the filtered solution into vials; stoppering and sealing the vials and storing the vials in suitable shipper, e) inert gas such as nitrogen is used throughout the process to reduce the risk of oxidation of carfilzomib.

Sterilization can be achieved by gamma-irradiation, e-beam, natural light, filtration, microwave heat sterilization such as moist heat sterilization. The sterilization may be steam sterilization or may be heat sterilization or filtration sterilization or a combination thereof.

In one embodiment, the present invention provides stable, ready-to-use compositions which may be sterilized by filtration, heat sterilization, radiation (gamma-irradiation, electron beam, microwave) ethylene oxide sterilization and the like. Filtration is performed through filters with pore size ranging from 0.2 μm to 0.5 μm.

Regardless of the particular composition, it is preferred that the composition is packaged in a container suitable for single or multiple-use. Such containers include an ampoule, vials, a pre-filled syringe, an intravenous bag and the like. Multi-dose containers may contain the carfilzomib in an amount suitable to allow one or more distinct uses (based on the requirement to the user). Thus, preferred multi-dose containers will be configured to contain a volume of the composition that is suitable for multiple and independent administrations.

Carfilzomib with or without other therapeutically active agents may also be used in combination or prior to administering carfilzomib composition without departing from the present invention or to prevent side effects (e.g., hypersensitivity reactions, gastrointestinal symptoms) associated with the administration of the inventive compositions. These agents may optionally be added to the compositions. Preferably the therapeutically active agents synergistically enhance the effect of carfilzomib. Examples of therapeutic agents that may be used in conjunction with the pharmaceutical compositions of the present invention include, but are not limited to alkylating agents, antihistamines, hormonal agents, $H_2$ antagonists, plant-derived agents, biologic agents, thalidomides or its derivatives, steroids or its derivatives, interleukins, interferons, cytokines, immuno-modulating agents, monoclonal antibodies, natural product, anticancer agents, histone deacetylase inhibitors, antiretroviral agents, platinum-based drugs, and combinations thereof.

In one more embodiment the present invention relates to provide a stable ready-to-use composition to treat patients in need thereof for the treatment of multiple myeloma, lymphoma, leukemia, carcinoma or related conditions.

To further illustrate the invention, the following examples are provided. It is to be understood that these examples are provided for illustrative purposes and are not to be construed as limiting the scope of the invention. It is to be further understood that, in the examples the functions of individual ingredients are sometimes listed for illustration purposes.

EXAMPLES

Proposed carfilzomib compositions were developed and tested for feasibility as semi-aqueous compositions, non-aqueous compositions with non-volatile sugar acids, acidifying agent with or without any excipients to check the physico-chemical parameters and its stability. Semi-aqueous compositions were developed and found clear as such and on dilution with physiological solution thereby indicating physical stability, hence these compositions were tested for chemical stability. However, semi aqueous compositions degraded in presence of water, observed known and unknown impurities were at higher side. Further it was understood that composition containing aqueous portion may lead to hydrolysis, therefore it was concluded that compositions should be free from water. Hence non-aqueous compositions were developed and the same are exemplified below:

Example 1: Non-Aqueous Compositions

| Sl. No | Ingredients | NAQ1 | NAQ2 | NAQ3 | NAQ4 | NAQ5 |
|---|---|---|---|---|---|---|
| | | Quantity (mg/mL) | | | | |
| 1. | Carfilzomib | 10 | 10 | 10 | 10 | 10 |
| 2. | Ascorbic acid | 3 | — | — | — | — |
| 3. | Citric acid | — | 10 | 10 | — | — |
| 4. | PEG 300 | 350 | 300 | 300 | — | 150 |
| 5. | Propylene Glycol | Qs to 1 mL | 300 | — | 150 | |
| 6. | Polysorbate 80 | — | 100 | 300 | — | |
| 7. | Alpha-tocopherol | — | — | 0.2 | 0.2 | |
| 8. | Ethanol | — | Qs to 1 mL | Qs to 1 mL | Qs to 1 mL | |

Example 1: Continued

| Sl. No | Ingredients | NAQ6 | NAQ7 | NAQ8 | NAQ9 |
|---|---|---|---|---|---|
| | | Quantity (mg/mL) | | | |
| 1. | Carfilzomib | 10 | 10 | 10 | 10 |
| 2. | PEG 300 | 200 | 200 | — | 150 |
| 3. | Propylene Glycol | 200 | 200 | — | 150 |
| 4. | Polysorbate 80 | 100 | 300 | 100 | 300 |
| 5. | Alpha-tocopherol | — | — | 0.2 | 0.2 |
| 6. | Sulphuric acid | Qs to pH | — | — | — |
| 7. | Ethanoic acid | — | — | Qs to pH | |
| 8. | Ethanol | Qs to 1 mL | | Qs to 1 mL | Qs to 1 mL |

Considering the semi-aqueous compositions results, non-aqueous compositions were developed to check the feasibility and stability of same.

Non-aqueous compositions NAQ1 comprising ascorbic acid were clear as such initially and turned hazy later, hence NAQ1 compositions were discontinued from further studies. Non-aqueous compositions NAQ2 and NAQ3 compositions comprising citric acid were clear initially and later turned hazy, hence NAQ2 and NAQ3 compositions were discontinued from further studies. NAQ4 & NAQ5 compositions devoid of any non-volatile sugar acid were developed and initially the compositions were clear and slowly developed haziness, forcing to discontinue with further studies.

Considering above observations on clarity of drug solution, few other compositions were developed with acidifying agent such as sulphuric acid, ethanoic acid. NAQ6 and NAQ7 drug solution compositions with sulphuric acid and NAQ8, NAQ9 compositions with ethanoic acid were clear for prolonged time and hence these compositions were considered for further studies.

Example 2: Compositions With Sulphuric Acid

| Sl. No | Ingredients | AA1 | AA2 | AA3 | AA4 | AA5 | AA6 | AA7 |
|---|---|---|---|---|---|---|---|---|
| | | Quantity (mg/mL) | | | | | | |
| 1. | Carfilzomib | 10 | 10 | 10 | 10 | 10 | 10 | 10 |
| 2. | Propylene Glycol | 150 | 200 | 200 | 200 | — | — | — |
| 3. | PEG 300 | 150 | 200 | 200 | 200 | — | — | — |
| 4. | Polysorbate 80 | 300 | 100 | 200 | 300 | 100 | 200 | 300 |
| 5. | Alpha-tocopherol | 0.2 | — | — | — | — | — | — |
| 6. | Sulphuric acid | Qs to pH | | | | | | |
| 7. | Ethanol | Qs to 1 mL | | | | | | |

TABLE 2

Physical Observations

| Composition | Description | Physio. solution description (mg/mL) | | | | Remarks |
| --- | --- | --- | --- | --- | --- | --- |
| | | WFI | | 5% dextrose | | |
| | | 0.2 | 0.5 | 0.2 | 0.5 | |
| AA1 | CS | CS | CS | CS | CS | Physiological solution was clear free from particles |
| AA2 | CS | LH | H | LH | H | Physiological solution turned hazy after dilution |
| AA3 | CS | LH | H | LH | H | Physiological solution was clear for two hours after dilution with composition |
| AA4 | CS | CS | CS | CS | CS | Physiological solution was clear free from particles |
| AA5 | CS | LH | H | LH | H | Physiological solution turned hazy after dilution |
| AA6 | CS | LH | H | LH | H | Physiological solution turned hazy after dilution |
| AA7 | CS | CS | CS | CS | CS | Physiological solution was clear free from particles |

CS—Clear Solution;
LH—Light Hazy;
H—Hazy

Considering the drug solution clarity, compositions with sulphuric acid were developed to check the stability. Example 3 discloses that few proposed compositions containing sulphuric acid were clear, free from the particles and the pH was recorded towards acidic side a noteworthy indication. However physiological solution turned hazy after dilution with few other compositions containing less than or equal to 200 mg/mL polysorbate 80. It was confirmed that propylene glycol and PEG 300 content in the composition had negligible role to play. Hence AA1, AA4 and AA7 compositions were considered for further stability studies.

Example 3- Compositions With Ethanoic Acid

| Sl. No | Ingredients | AA8 | AA9 | AA10 | AA11 | AA12 | AA13 | AA14 |
| --- | --- | --- | --- | --- | --- | --- | --- | --- |
| | | Quantity (mg/mL) | | | | | | |
| 1. | Carfilzomib | 10 | 10 | 15 | 10 | 10 | 10 | 10 |
| 2. | Polysorbate 80 | — | — | — | 400 | 500 | 200 | 300 |
| 3. | Ethanoic acid | — | 150 | 30 | 10 | 20 | 30 | 30 |
| 4. | Alpha-tocopherol | — | — | — | — | — | — | 0.2 |
| 5. | Ethanol | Qs to 1 mL | | | | | | |

| Sl. No | Ingredients | AA15 | AA16 | AA17 | AA18 | AA19 | AA20 | AA21 |
| --- | --- | --- | --- | --- | --- | --- | --- | --- |
| | | Quantity (mg/mL) | | | | | | |
| 1. | Carfilzomib | 10 | 10 | 20 | 20 | 20 | 10 | 20 |
| 2. | Polysorbate 80 | 400 | 400 | — | — | — | 300 | 400 |
| 3. | Ethanoic acid | 30 | 50 | 50 | 100 | 150 | 30 | 30 |
| 4. | Alpha-tocopherol | — | — | — | — | — | 0.2 | 0.2 |
| 5. | Ethanol | Qs to 1 mL | | | | | | |

TABLE 3

Physical Observations

| Composition | Description | Physio. solution description (mg/mL) | | | | Remarks |
| --- | --- | --- | --- | --- | --- | --- |
| | | WFI | | 5% dextrose | | |
| | | 0.2 | 0.5 | 0.2 | 0.5 | |
| AA8 | CS | H | H | H | H | Immediately after dilution, clear solution turned hazy |
| AA9 | CS | CS | CS | CS | CS | Physiological solution was clear free from particles after dilution |

TABLE 3-continued

Physical Observations

| | | Physio. solution description (mg/mL) | | | | |
|---|---|---|---|---|---|---|
| | | WFI | | 5% dextrose | | |
| Composition | Description | 0.2 | 0.5 | 0.2 | 0.5 | Remarks |
| AA10 | CS | LH | H | LH | H | Physiological solution turned hazy after dilution |
| AA11 | CS | LH | H | LH | H | Physiological solution turned hazy after dilution |
| AA12 | CS | LH | H | LH | H | Physiological solution turned hazy after dilution |
| AA13 | CS | LH | H | LH | H | Physiological solution turned hazy after dilution |
| AA14 | CS | LH | H | LH | H | Physiological solution turned hazy after dilution |
| AA15 | CS | CS | CS | CS | CS | Physiological solution was clear free from particles after dilution |
| AA16 | CS | CS | CS | CS | CS | Physiological solution was clear free from particles after dilution |
| AA17 | CS | CS | CS | CS | CS | Physiological solution turned hazy after dilution |
| AA18 | CS | CS | CS | CS | CS | Physiological solution turned hazy after dilution |
| AA19 | CS | CS | CS | CS | CS | Physiological solution turned hazy after dilution |
| AA20 | CS | CS | CS | CS | CS | Physiological solution was clear free from particles after dilution |
| AA21 | CS | LH | H | LH | H | Physiological solution turned hazy after dilution |

The above examples were studied for optimizing ethanoic acid and polysorbate 80 concentration in the composition to check the physical stability after dilution with physiological solution. From the above observations it was accomplished that the proposed compositions AA15 and AA16 with 10 mg/mL carfilzomib were clear and free from the particles, even after dilution with physiological solution. However, AA17, AA18, AA19 and AA21 compositions with 20 mg/mL carfilzomib concentration and with or without polysorbate 80 were tested and all compositions turned hazy on dilution with physiological solution thereby endorsing physical instability. Further AA10, 15 mg/mL concentration of carfilzomib compositions also turned hazy, hence 15 mg/mL and 20 mg/mL compositions were discontinued from further stability studies. Other compositions with reduced ethanoic acid and polysorbate 80 concentration turned hazy after dilution with physiological solution. Hence AA9, AA15, AA16 and AA20 compositions which were clear upon dilution with physiological solution were considered for further studies.

Example 4- Impact of Ethanoic Acid Quantity on CHEMICAL Stability

| Sl. No | Ingredients | EA1 | EA2 | EA3 | EA4 | EA5 | EA6 |
|---|---|---|---|---|---|---|---|
| | | | | Quantity (mg/mL) | | | |
| 1. | Carfilzomib | 10 | 10 | 10 | 10 | 10 | 10 |
| 2. | Polysorbate 80 | 300 | 300 | 300 | 300 | 300 | 300 |
| 3. | Propylene Glycol | — | — | — | — | — | — |
| 4. | PEG 300 | — | — | — | — | — | — |
| 5. | Alpha-tocopherol | 0.2 | 0.2 | 0.2 | 0.2 | 0.2 | 0.2 |
| 6. | Ethanoic acid | 150 | 100 | 50 | 30 | 20 | 10 |
| 7. | Ethanol | | | Qs to 1 mL | | | |

TABLE 4

Chemical Stability of EA1, EA2, EA3, EA4, EA5 and EA6 compositions

| | | Parameters | | | | | |
|---|---|---|---|---|---|---|---|
| Time Points | Time (Days) | EA1 | EA2 | EA3 | EA4 | EA5 | EA6 |
| | | | | Total Impurities (%) | | | |
| 60° C. | 3 days | 4.1 | 3.78 | 2.81 | 2.66 | 2.22 | 2.1 |

From the above example, 6 compositions EA1, EA2, EA3, EA4, EA5 and EA6 were tested for stability with varying concentration of ethanoic acid at stress condition to know the stability, it was accomplished that compositions degradation is proportional to the quantity of ethanoic acid. Hence considering chemical stability parameters of above compositions, it was inferred that polysorbate 80 and ethanoic acid quantity needs to be optimized in order to stabilize the composition. Further, from the physical stability studies, it has been concluded that AA9, AA15, AA16 and AA20 compositions were physically stable as they were clear upon dilution with physiological solution. Therefore, considering chemical and physical stability outcome the, below composition was optimized.

Example 5: Optimized Composition

| Sl. No | Ingredients | Quantity (mg/mL) |
|---|---|---|
| 1. | Carfilzomib | 10 |
| 2. | Polysorbate 80 | 300 |
| 3. | Alpha-tocopherol | 0.2 |
| 4. | PEG 300 | 100 |
| 5. | Ethanoic acid | 30 |
| 6. | Ethanol | Qs to 1 mL |

TABLE 5

Chemical Stability of Optimized composition

| | Parameters | |
|---|---|---|
| Time Points | Time (Months) | Total Impurities (%) |
| $T_0$ | $T_0$ | 0.06 |
| 2-8° C. | 1 M | 0.07 |
| 25° C./60 RH | 1 M | 0.43 |
| 40° C./75 RH | 1 M | 1.56 |

Based on the physicochemical stability details, composition of example 5 were developed to optimize quantities of ethanoic acid required to stabilize the carfilzomib non-aqueous ready-to-use composition. Considering the above composition stability data, it is inferred that composition degradation is proportional to the quantity of ethanoic acid in the composition.

Therefore, considering the above examples 1 to 5 it is accomplished that optimum quantity of ethanoic acid and optimum quantity of polysorbate 80 is required for both physical and chemical stability of the non-aqueous compositions, apart from other excipients in the compositions. Numerous trials have been performed to determine the effect of ethanoic acid quantity on formulation stability and parallel physical stability with combination of surfactant, from the physical stability data it was concluded that equal to or more than 30 mg ethanoic acid was required to keep the diluted solution stable for at least 24 hours or more with the help of surfactant. The observed formulation degradation rate is directly propositional to the quantity of ethanoic acid in the formulation. However, surfactant did not show any significant impact on chemical stability, but played critical role on physical stability, the minimum quantity of surfactant 300 mg is required to keep the diluted solution clear for at least 24 hours and above with the help of ethanoic acid. However, ethanoic acid comprising compositions are comparable to each other both physically and chemically thereby producing stable, ready-to-use, non-aqueous compositions.

The ready-to-use compositions are stable at 2° C. to 25° C., and room temperature for at least 3 months.

We claim:

1. A liquid composition comprising:
carfilzomib in an amount of about 1 mg/mL to about 20 mg/mL or a pharmaceutically acceptable salt thereof;
ethanoic acid, wherein a ratio of the ethanoic acid to the carfilzomib is 1.5:1 to 10:1;
at least one solvent;
at least one surfactant selected from the group consisting of a polyoxyethylene sorbitan ester, a polyoxyethylene polyoxypropylene copolymer, a sorbitan ester, lecithin, cremophor, and mixtures thereof, wherein the at least one surfactant is included in an amount of at least about 300 mg/mL; and
an anti-oxidant,
wherein the liquid composition is stable, ready to dilute, and non-aqueous.

2. The liquid composition according to claim 1, wherein the at least one solvent comprises at least one of an alcohol, a glycol, glycerol or a derivative thereof, and mixtures thereof.

3. The liquid composition according to claim 2, wherein the glycol is at least one of propylene glycol, polyethylene glycol, and mixtures thereof and the alcohol is at least one of ethanol, butanol, t-butanol, and mixtures thereof.

4. The liquid composition according to claim 1, wherein the anti-oxidant is at least one of monothioglycerol, alpha-tocopherol, L-cysteine, thioglycolic acid, sodium metabisulfite, ascorbic acid, sodium formaldehyde sulfoxylate, sodium bisulfate, butylated hydroxy toluene, butylated hydroxy anisole, and mixtures thereof.

5. The liquid composition of claim 1, wherein the anti-oxidant is alpha-tocopherol; the surfactant is a polyoxyethylene sorbitan ester; and the solvent is glycerol, propylene glycol, polyethylene glycol, ethanol, butanol, t-butanol, and mixtures thereof.

6. The liquid composition according to claim 5, wherein the liquid composition is ready to dilute; is stable when stored at 25° C., 60% relative humidity for at least 1 month, is clear upon dilution with a physiological solution and is stable when diluted for at least about 24 hours.

7. The liquid composition of claim 1, wherein the composition is free of non-volatile sugar acid.

8. A liquid composition comprising:
carfilzomib in an amount of about 1 mg/mL to about 20 mg/mL or a pharmaceutically acceptable salt thereof;
ethanoic acid, wherein the ratio of the ethanoic acid to the carfilzomib is about 1.5:1 to about 10:1;
at least one solvent;
at least one surfactant selected from the group consisting of a polyoxyethylene sorbitan ester, a polyoxyethylene polyoxypropylene copolymer, a sorbitan ester, lecithin, cremophor, and mixtures thereof, wherein the at least one surfactant is included in an amount of at least about 300 mg/mL; and
an antioxidant,
wherein the liquid composition is non-aqueous,
wherein the liquid composition is ready to dilute and the liquid composition is clear upon dilution with physiological solution and stable for at least about 24 hours, and has a pH is from about 2 to about 9.

9. The liquid composition according to claim 8, wherein the composition is stable when stored at 25° C., 60% relative humidity for at least 1 month.

10. A composition comprising:
carfilzomib or a pharmaceutically acceptable salt thereof present in an amount of about 10 mg/mL,
ethanoic acid present in an amount of about 30 mg/mL,
at least one solvent,
polysorbate 80 present in an amount of about 300 mg/mL, and
alpha-tocopherol present in an amount of about 0.2 mg/mL,
and
wherein the composition is stable, ready to use, and non-aqueous.

11. A method for treating multiple myeloma comprising administering the composition according to claim 1 in a parenteral dosage form.

\* \* \* \* \*